US009471541B1

(12) United States Patent
Chan et al.

(10) Patent No.: US 9,471,541 B1
(45) Date of Patent: Oct. 18, 2016

(54) DETERMINING A TIME PERIOD A PERSON IS IN BED

(71) Applicant: Vital Connect, Inc., Campbell, CA (US)

(72) Inventors: Alexander Chan, Campbell, CA (US); Ravi Narasimhan, Sunnyvale, CA (US)

(73) Assignee: Vital Connect, Inc., Campbell, CA (US)

( * ) Notice: Subject to any disclaimer, the term of this patent is extended or adjusted under 35 U.S.C. 154(b) by 573 days.

(21) Appl. No.: 13/941,387

(22) Filed: Jul. 12, 2013

(51) Int. Cl.
*G04F 13/04* (2006.01)
*G07C 1/00* (2006.01)
*A61B 5/00* (2006.01)
*A61B 5/11* (2006.01)
*G01P 15/00* (2006.01)
*G01D 21/00* (2006.01)
*G06F 17/40* (2006.01)
*G06F 19/00* (2011.01)
*G06F 17/00* (2006.01)

(52) U.S. Cl.
CPC ............... *G06F 17/00* (2013.01); *G04F 13/04* (2013.01); *G07C 1/00* (2013.01); *A61B 5/00* (2013.01); *A61B 5/11* (2013.01); *G01D 21/00* (2013.01); *G01P 15/00* (2013.01); *G06F 17/40* (2013.01); *G06F 19/00* (2013.01)

(58) Field of Classification Search
None
See application file for complete search history.

(56) References Cited

U.S. PATENT DOCUMENTS

| | | | |
|---|---|---|---|
| 6,044,297 A | 3/2000 | Sheldon et al. | |
| 6,494,850 B1 * | 12/2002 | Kitadou | A47C 3/02 601/49 |
| 6,695,799 B2 * | 2/2004 | Kitadou | A47C 3/02 601/49 |
| 9,028,407 B1 * | 5/2015 | Bennett-Guerrero | A61B 5/1121 224/929 |
| 9,035,794 B2 * | 5/2015 | Narasimhan | G01C 25/00 340/870.2 |
| 2002/0183667 A1 * | 12/2002 | Kitadou | A47C 3/02 601/91 |
| 2007/0032733 A1 * | 2/2007 | Burton | A61B 5/02405 600/509 |
| 2007/0115277 A1 | 5/2007 | Wang et al. | |
| 2010/0010583 A1 | 1/2010 | Panken et al. | |
| 2010/0298655 A1 | 11/2010 | McCombie et al. | |
| 2011/0172927 A1 | 7/2011 | Sahasrabudhe et al. | |
| 2011/0201969 A1 | 8/2011 | Hatlestad et al. | |
| 2011/0241656 A1 | 10/2011 | Piemonte et al. | |
| 2012/0101411 A1 | 4/2012 | Hausdorff et al. | |
| 2012/0203487 A1 | 8/2012 | Johnson et al. | |
| 2013/0090881 A1 * | 4/2013 | Janardhanan | G01C 22/006 702/104 |
| 2013/0274830 A1 | 10/2013 | Skelton | |
| 2014/0015687 A1 * | 1/2014 | Narasimhan | G01C 25/00 340/870.02 |
| 2014/0019080 A1 * | 1/2014 | Chan | G01P 21/00 702/104 |
| 2014/0066816 A1 * | 3/2014 | McNames | A61B 5/002 600/595 |
| 2014/0128778 A1 * | 5/2014 | Chan | A61B 5/1116 600/595 |
| 2015/0190086 A1 * | 7/2015 | Chan | A61B 5/4812 600/301 |
| 2015/0257654 A1 * | 9/2015 | Bennett-Guerrero | A61B 5/1121 600/301 |

OTHER PUBLICATIONS

The International Search Report and the Written Opinion of the International Searching Authority, issued for International Application No. PCT/US2013/045321, mailed on Dec. 2, 2013.

\* cited by examiner

*Primary Examiner* — Edward Cosimano
(74) *Attorney, Agent, or Firm* — Brundidge & Stanger, P.C.

(57) ABSTRACT

A method and wireless sensor device for determining a time period a person is in bed. In one aspect, a method includes utilizing a wireless sensor device to obtain a plurality of acceleration samples in relation to at least one axis associated with a person's body over a predetermined time window. The method also includes calculating a polar angle for each acceleration sample within the predetermined time window. The method also includes calculating a fraction of an amount of time within the predetermined time window that the polar angle is greater than an angle threshold that indicates that the person is lying down, where if the fraction is greater than a predetermined threshold, the predetermined time window is marked as a period the person is lying down.

20 Claims, 7 Drawing Sheets

600

US 9,471,541 B1

DETERMINING A TIME PERIOD A PERSON IS IN BED

CROSS-REFERENCE TO RELATED APPLICATIONS

The present invention is related to U.S. patent application Ser. No. 13/900,438, filed on May 22, 2013, entitled "CALIBRATION OF A CHEST-MOUNTED WIRELESS SENSOR DEVICE FOR POSTURE AND ACTIVITY DETECTION," and to U.S. patent application Ser. No. 13/548,059, filed Jul. 12, 2012, now U.S. Pat. No. 9,035,794, entitled "POSTURE CALIBRATION FOR ACTIVITY MONITORING," all of which are herein incorporated by reference in their entireties.

FIELD OF THE INVENTION

The present invention relates generally to wireless sensor devices, and more particularly to a wireless sensor device for determining a time period a person is in bed.

BACKGROUND

Wireless sensor devices are used in a variety of applications including the posture detection and activity monitoring of users. In many of these applications, a wireless sensor device is attached directly to the user's skin (e.g., near the chest area) to measure certain data. This measured data is then utilized for the posture detection and activity monitoring of the users. There is a strong need for a cost-effective solution that overcomes the aforementioned issues. The present invention addresses such a need.

SUMMARY

A method and wireless sensor device for determining a time period a person is in bed are disclosed. In one aspect, a method includes utilizing a wireless sensor device to obtain a plurality of acceleration samples in relation to at least one axis associated with a person's body over a predetermined time window. The method also includes calculating a polar angle for each acceleration sample within the predetermined time window. The method also includes calculating a fraction of an amount of time within the predetermined time window that the polar angle is greater than an angle threshold that indicates that the person is lying down, where if the fraction is greater than a predetermined threshold, the predetermined time window is marked as a period the person is lying down.

In another aspect, a wireless sensor device includes a processor and a memory device coupled to the processor. The wireless sensor device includes an application that, when executed by the processor, causes the processor to perform operations including obtaining a plurality of acceleration samples in relation to at least one axis associated with a person's body over a predetermined time window utilizing a wireless sensor device to obtain the plurality of acceleration samples; calculating a polar angle for each acceleration sample within the predetermined time window; and calculating a fraction of an amount of time within the predetermined time window that the polar angle is greater than an angle threshold that indicates that the person is lying down, and wherein if the fraction is greater than a predetermined threshold, the predetermined time window is marked as a period the person is lying down.

DETAILED DESCRIPTION

The present invention relates generally to wireless sensor devices, and more particularly, to a wireless sensor device for determining a time period a person is in bed. The following description is presented to enable one of ordinary skill in the art to make and use embodiments of the invention, and is provided in the context of a patent application and its requirements. Various modifications to the embodiments and the generic principles and features described herein will be readily apparent to those skilled in the art. Thus, embodiments of the present invention are not intended to be limited to the examples shown, but are to be accorded the widest scope consistent with the principles and features described herein.

Embodiments provide a method and system for determining a time period a person is in bed. Embodiments use a wireless sensor device such as an accelerometer that is mounted on the chest or torso of a person to measure a variety of sleep parameters that can be important for monitoring sleep patterns. The accelerometer on the chest can be used to determine a time of bed entry, a time of bed exit, and total time in bed. These parameters are useful for tracking aspects such as the general regularity of the sleep time over a course of days or months. These parameters can also be used to trigger start and end of algorithms that are run during sleep in order to understand and monitor general sleep patterns (e.g., sleep staging, sleep apnea detection). For example, if a bed entry is detected, embodiments may start a sleep staging algorithm (e.g., whether you are in deep sleep, light sleep, rapid eye movement (REM) like dreaming), a sleep apnea detection algorithm, a stress analysis during sleep, etc. Embodiment may also look for resting heart rate.

As described in more detail below, a wireless sensor device obtains acceleration samples in relation to one or more axes associated with a person's body over a predetermined time window. The wireless sensor device calculates a polar angle for each acceleration sample within the predetermined time window. Next, the wireless sensor device calculates a fraction of an amount of time within the predetermined time window that the polar angle is greater than an angle threshold that indicates that the person is lying down. In one embodiment, if the fraction is greater than a predetermined threshold, the predetermined time window is marked as a period the person is lying down.

Figure 1:
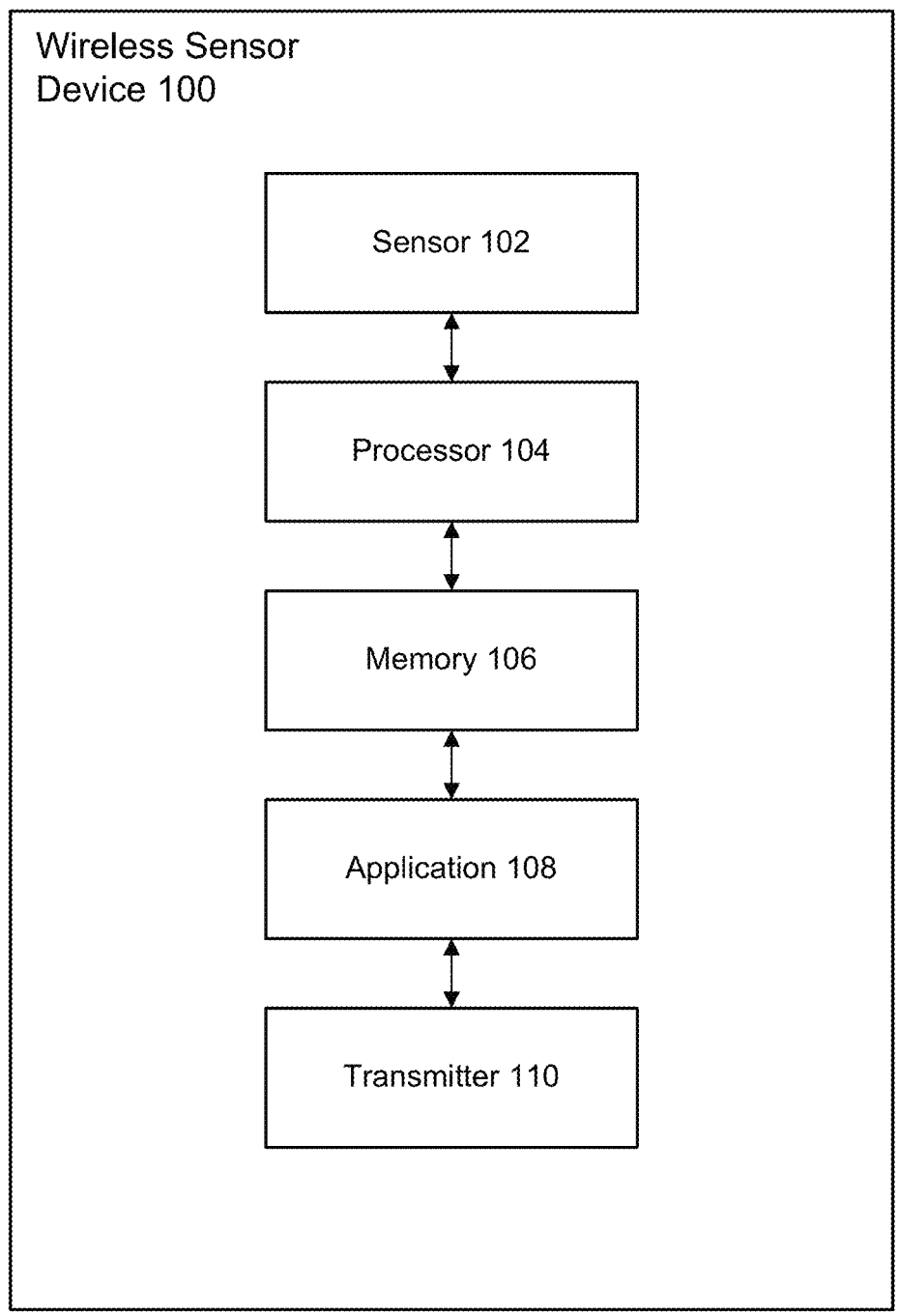
FIG. 1 illustrates a wireless sensor device in accordance with an embodiment.

FIG. 1 illustrates a wireless sensor device 100 in accordance with an embodiment. As shown, the wireless sensor device 100 includes a sensor 102, a processor 104 coupled to the sensor 102, a memory 106 coupled to the processor 104, an application 108 coupled to the memory 106, and a transmitter 110 coupled to the application 108. In one embodiment, the wireless sensor device 100 is attached, in any orientation to a user and on any location of the user. In one embodiment, the wireless sensor device 100 is chest- or torso- or thorax-mounted to the user. The sensor 102 obtains data from the user and transmits the data to the memory 106 and in turn to the application 108. The processor 104 executes the application 108 to monitor information regarding the user's posture and activity levels. The information is transmitted to the transmitter 110 and in turn relayed to another user or device.

In one embodiment, the sensor 102 is a microelectromechanical system (MEMS) tri-axial accelerometer and the processor 104 is a microprocessor. One of ordinary skill in the art readily recognizes that a variety of devices can be utilized for the processor 104, the memory 106, the application 108, and the transmitter 110 and that would be within the spirit and scope of the present invention.

In one embodiment, the wireless sensor device includes a triaxial accelerometer. One of ordinary skill in the art readily recognizes that a variety of wireless sensor devices can be utilized. For example, various embodiments, the wireless sensor device may be at least one of a triaxial accelerometer, a uni-axial accelerometers, a bi-axial accelerometers, a gyroscope, a pressure sensor, a patch form-factor, etc., all of which would be within the spirit and scope of the embodiments of the present invention.

In one embodiment, the acceleration samples are calibrated. Conventionally, a wireless sensor device that only utilizes non-calibrated accelerometer data leads to less accurate posture detection and activity level monitoring. Non-calibrated accelerometer data can be arbitrarily positioned relative to the actual body axes. Therefore, embodiments described herein may involve a calibration procedure of the wireless sensor device that enables the generation of three derived axes of acceleration data that line up with actual body axes: anterior-posterior AP (front-to-back)—Z-axis; medial-lateral ML (left-to-right)—X-axis; and vertical VT (head-to-toe)—Y-axis. The calibration procedure requires determining at least the direction of the VT axis before the VT axis is then used to determine the other 2 axes. In another embodiment, additional calibration during leaning forward or lying supine is utilized to improve calibration accuracy.

Embodiments calibrate a wireless sensor device via automatic calibration, manual calibration, and sleep study calibration. In automatic calibration, an algorithm analyzes whether the user is walking and then obtains a vertical calibration vector during this detected walking period. In manual calibration, there is a wireless communication between the patch form-factor wireless sensor device and a relay (e.g., smartphone, handheld device, computer, communication device) that manually calibrates the wireless sensor device when selected or when automatic calibration fails. Manual calibration includes but is not limited to single upright calibration, walking calibration, upright and leaning forward calibration for improved accuracy, and supine and sitting up calibration for bedridden patients. In sleep study calibration, if only sleep data when the user is lying down is available (e.g. during a sleep study), an algorithm automatically calibrates the wireless sensor device given a whole night of data.

Embodiments determine a vertical axis VT and use the VT to determine the other 2 axes. If manual calibration is selected, all of the microelectromechanical systems (MEMS) based algorithms of the wireless sensor device utilize the manual calibration to detect posture and activity levels of the user. If automatic calibration is selected, all of the MEMS based algorithms of the wireless sensor device utilize the automatic calibration to detect posture and activity levels of the user. If neither manual calibration nor automatic calibration is selected, posture detection is disabled and all of the MEMS based algorithms of the wireless sensor device operate in non-calibrated mode.

Once automatic calibration of the wireless sensor device is achieved, the derived calibration vector enables the wireless sensor device to utilize various algorithms that measure the user's activity levels including but not limited to pedometer activity, fall detection, and posture detection. In one embodiment, after attaching the wireless sensor device to the user, the wireless sensor device continuously and automatically obtains varying types of data including but not limited to acceleration samples along the vertical axis of the user. An application embedded within a processor of the wireless sensor device compares the acceleration samples to a threshold to measure the user's activity levels.

Figure 2:
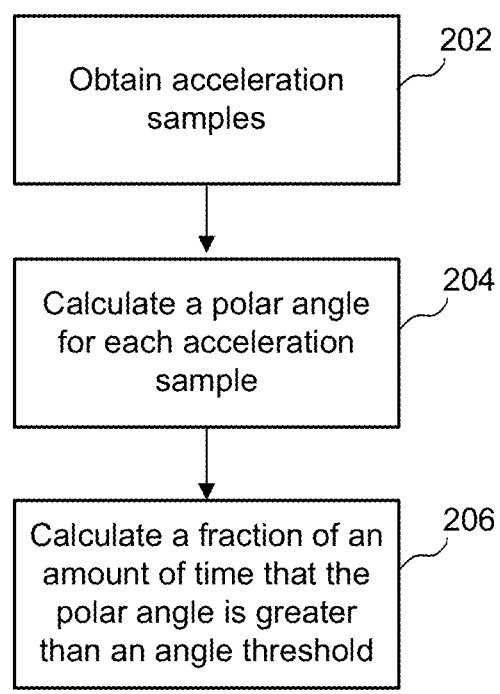
FIG. 2 illustrates a method for determining a time period a person is in bed in accordance with an embodiment.

FIG. 2 illustrates a method for determining a time period a person is in bed in accordance with an embodiment. Referring to FIGS. 1 and 2 together, first, the wireless sensor device 100 obtains acceleration samples in relation to at least one axis associated with a person's body over a predetermined time window, via step 202.

In one embodiment, the at least one axis includes a plurality of axes in relation to the person's body. For example, in one embodiment, the at least one axis includes one or more of an X-axis, a Y-axis, and a Z-axis in relation to the person's body. In one embodiment, the at least one axis includes one or more of an X-axis, a Y-axis, and a Z-axis, and wherein the X-axis is a mediolateral axis (e.g., left-to-right), the Y-axis is a vertical axis (e.g., head-to-toe), and the Z-axis is an anteroposterior axis (e.g., front-to-back) in relation to the person's body.

In one embodiment, the obtaining of the plurality of acceleration samples may includes the wireless sensor device 100 obtaining raw acceleration samples in relation to the at least one axis, and determining the plurality acceleration samples based on calibrated raw acceleration samples. Further embodiments for obtaining acceleration samples are described in more detail below, in connection with FIG. 4.

In example scenario, the wireless sensor device 100 obtains x-, y-, z-accelerations for a window length of T (e.g., T=600 seconds, or 10 minutes). These accelerations are calibrated x-, y-, z-accelarations.

Next, the wireless sensor device 100 calculates a polar angle for each acceleration sample within the predetermined time window, via step 204. In various embodiments, the polar angle is an angle of the person's body with respect to gravity.

Figure 3:
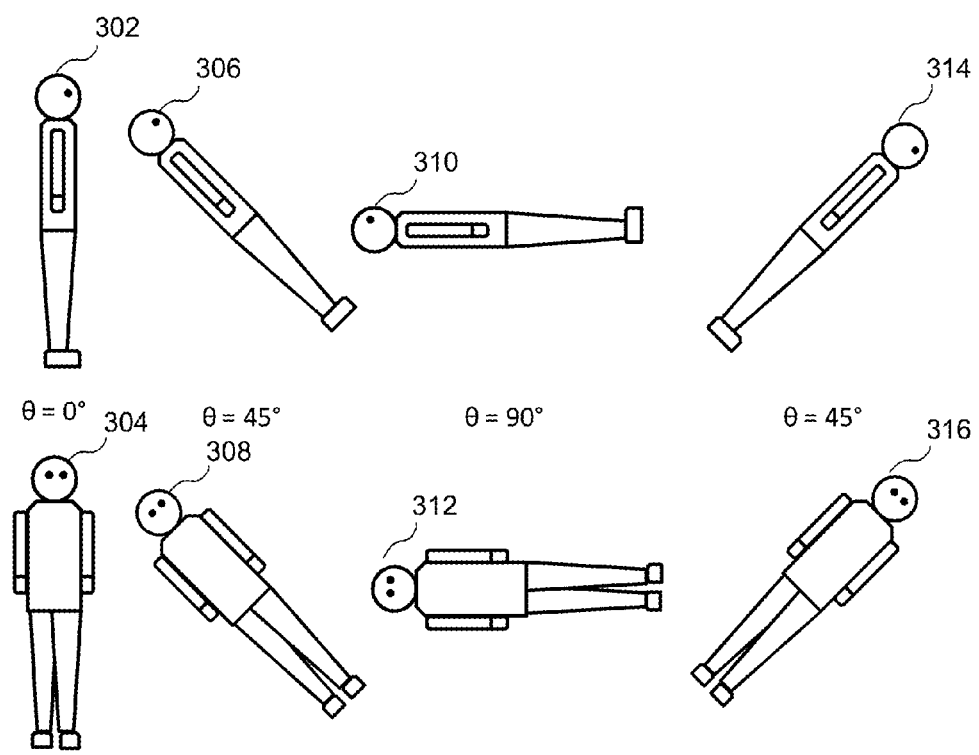
FIG. 3 illustrates a diagram showing body positions in relation to a polar angle in accordance with an embodiment.

FIG. 3 illustrates a diagram 300 showing body positions in relation to a polar angle in accordance with an embodiment. Diagram 300 shows various scenarios to illustrate different polar angles θ. As shown, one example scenario shows a person in two body positions 302 and 304 where the polar angle is 0°. It does not matter which way the person is facing. Standing upright is 0°.

Another example scenario shows a person in four body positions 306, 308, 314, and 316 where the polar angle is 45°.

As shown, one example scenario shows a person in two body positions 310 and 312 where the polar angle is 90°.

Here, it does not matter whether the person is lying on the person's back, side, or front. Lying down completely flat is 90°.

Next, the wireless sensor device 100 calculates a fraction of an amount of time within the predetermined time window that the polar angle is greater than an angle threshold that indicates that the person is lying down, via step 206.

In one embodiment, if the fraction is greater than a predetermined threshold, the predetermined time window is marked as a period the person is lying down. Conversely, in one embodiment, if the fraction is less than the predetermined threshold, the predetermined time window is marked as a period the person is not lying down.

In one embodiment, a consecutive set of time windows all marked as lying down are referred to as a bed period having a bed entry time and a bed exit time. In one embodiment, multiple bed periods may be detected in a night, and the wireless sensor device 100 combines the multiple bed periods if an out-of-bed time between the bed periods is less than a combine threshold.

In an example scenario, in one embodiment, the wireless sensor device 100 compute the polar angle, $\theta[n]$, from the accelerations at each sample in the window: where $\theta[n]=\cos^{-1}(-A_y[n]/g)$, where $A_y[n]$ is (unnormalized) y-axis acceleration at sample n, and where g=9.81 m/s². In one embodiment, A[n] is a vector of the x-, y-, z-accelerations at sample n, where $A[n]=[A_X[n]\ A_Y[n]\ A_Z[n]]^T$. In one embodiment, the theta of sample N (e.g., polar angle of N), is the arc cosine of the negative acceleration in the y direction, normalized by G, where G is gravity, and $\theta[n]$ is the polar angle at sample n. The wireless sensor device 100 then computes the fraction of the window T (e.g., 600 second or 10 minutes) such that the polar angle, $\theta[n]$ is greater than an angle threshold, $\theta_{lie}$. The fraction of the window may be referred to as $F_{lie}$ where this polar angle is greater than the threshold angle (e.g., $\theta_{lie}$=40°). In other words, $F_{lie}$ indicates the fraction of the window T that the person is lying down.

In one embodiment, the fraction of an amount of time within the predetermined time window T that the polar angle is greater than an angle threshold (e.g., $\theta[n]>\theta_{lie}$) that indicates that the person is lying down may be referred to as the threshold fraction, or $F_{thresh}$. In one embodiment, if $F_{lie}>F_{thresh}$), the whole window T is marked as "lying down." For example, if $F_{thresh}$=0.95, the threshold requires that 95 percent of this window is lying down. As such, the person is considered lying down during the entire window for the purposes of subsequent determinations and calculations.

If this is the first window where this criteria being fulfilled, the bed entry time occurs within this window. In one embodiment, the bed entry time is computed as $(1-F_{thresh})*T*F_S$ samples from the start of this first window which is characterized as lying down, where $F_S$ is the sampling rate of the wireless sensor device (accelerometer) (e.g., time lying flat). In the case where $F_{thresh}$=0.95, the bed entry time occurs at 5 percent of the way through the window T, because threshold is set at 95 percent.

In one embodiment, the bed exit time occurs at $F_{thresh}*T*F_S$ samples from the start of the last window which is characterized as lying down. For example, the bed exit time occurs at 95 percent of the way towards the end of the window T, if the last window is characterized as lying down. In one embodiment, the time in bed is the exit time minus entry time (e.g., $Time_{in\ bed}=Time_{exit}-Time_{entry}$).

In one embodiment, the time in bed may be determined after collecting data for a predetermined time period (e.g., one night's data).

Further example embodiments directed to bed periods, bed entry times, and bed exit times is described in more detail below in connection with FIGS. 5 and 6.

Figure 4:
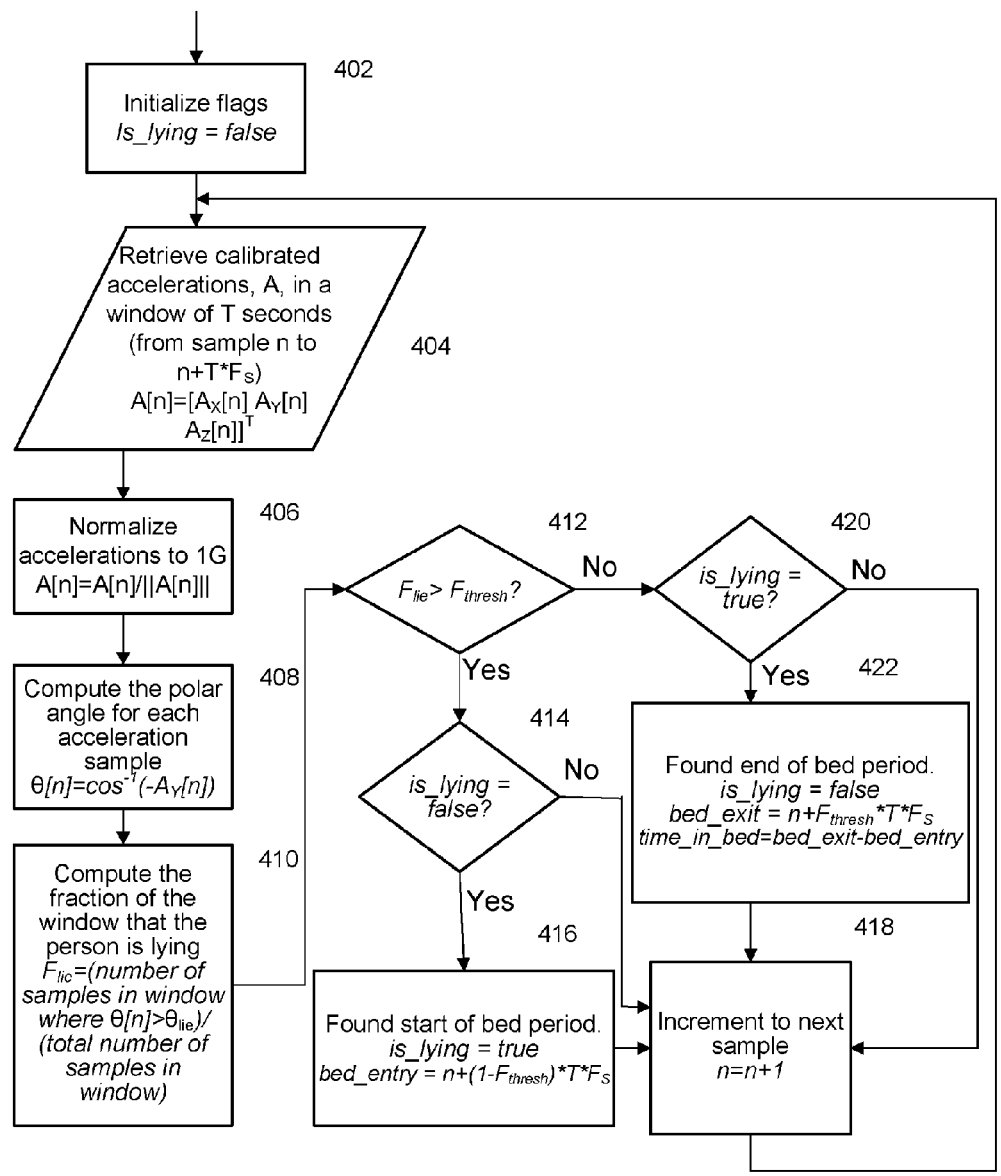
FIG. 4 illustrates a method for determining a time period a person is in bed in accordance with an embodiment.

FIG. 4 illustrates a method for determining a time period a person is in bed in accordance with an embodiment. This example method determines whether a person is lying or not for each window. Referring to FIGS. 1 and 4 together, first, the wireless sensor device 100 initializes flags, where is_lying=false, via step 402.

Next, the wireless sensor device 100 retrieves calibrated accelerations, A, in a window of T seconds (from sample n to n+T*$F_S$), where $A[n]=[A_X[n]\ A_Y[n]\ A_Z[n]]^T$, via step 404. For example, the window of T seconds could be a 600 second/ten minute window.

Next, the wireless sensor device 100 normalizes accelerations to 1G, where A[n]=A[n]/||A[n]||, via step 406. Next, the wireless sensor device 100 computes the polar angle for each acceleration sample, where $\theta[n]=\cos^{-1}(-A_y[n])$, via step 408. Next, the wireless sensor device 100 computes the fraction of the window that the person is lying, where $F_{lie}$=(number of samples in window where $\theta[n]>\theta_{lie}$)/(total number of samples in window), via step 410. Next, the wireless sensor device 100 determines if the person is lying down $F_{lie}>F_{thresh}$, via step 412. For example, the wireless sensor device 100 may determine that the person is lying down for the entire window, if $F_{lie}>F_{thresh}$, for greater than 95 percent of the window. If "yes," the wireless sensor device 100 determines if is_lying=false (if they were not lying before), via step 414. If is_lying=false, the wireless sensor device 100 found the start of bed period, and it sets is_lying=true, and bed_entry=n+(1-$F_{thresh}$)*T*$F_S$, via step 416. Next, the wireless sensor device 100 increment to next sample, where n=n+1, via step 418, and returns goes back to step 404. If in step 414, is_lying not=false, the wireless sensor device 100 increments to next sample, via step 418.

Referring again to step 412, if $F_{lie}$ is not>$F_{thresh}$, the wireless sensor device 100 determines if is_lying=true (if the person was lying before, in the previous sample), via step 420. If not, the wireless sensor device 100 increments to the next sample, via step 418.

If is_lying=true in step 420, the wireless sensor device 100 found the end of the bed period, via step 422, and sets is_lying=false, and bed_exit=n+$F_{thresh}$*T*$F_S$, and sets time_in_bed=bed_exit-bed_entry. Next, the wireless sensor device 100 increments to next sample, via step 418.

Figure 5:
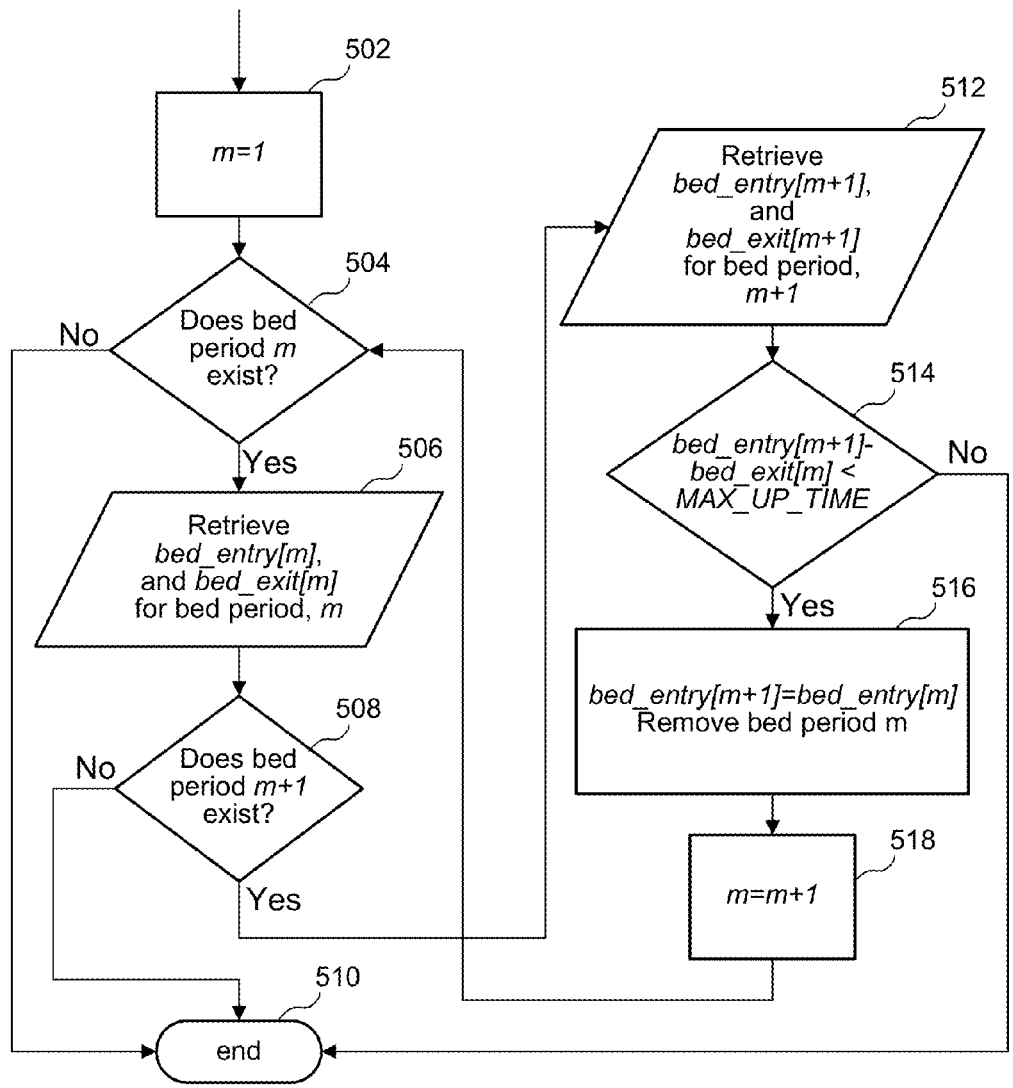
FIG. 5 illustrates a method for determining a time period a person is in bed in accordance with an embodiment.

FIG. 5 illustrates a method for determining a time period a person is in bed in accordance with an embodiment. This example method addresses when a person gets out of bed in the middle of the night, and returns within several minutes (e.g., to go to the bathroom). In one embodiment, these intervening periods may split a night into multiple bed periods. In one embodiment, bed periods may be combined by looking at the time between the end of one bed period and the start of the next bed period.

Referring to FIGS. 1 and 5 together, first, the wireless sensor device sets a first bed period m=1, via step 502. Next, the wireless sensor device 100 determines if a bed period m exists, via step 504. If "yes," the wireless sensor device 100 retrieves the bed entry data and bed exit data (e.g., bed_entry [m], and bed_exit[m]) for the bed period m, via step 506. Next, the wireless sensor device 100 determines if another bed period m+1 exists, via step 508. If "no" (no other bed period exists), the process ends, via step 510. Also, if, at step 504, a bed period m does not exist, the process ends, via step 510.

If, at step 508, the wireless sensor device 100 determines that another bed period m+1 exists, the wireless sensor device 100 retrieves bed entry data and bed exit data (e.g., bed_entry[m+1], and bed_exit[m+1] for bed period, m+1, via step 512.

Next, the wireless sensor device 100 determines if amount of time the person is out of bed does not exceed a maximum out-of-bed period (MAX_UP_TIME) (e.g., bed_entry[m+1]−bed_exit[m]<MAX_UP_TIME), via step 514. In other words, the wireless sensor device 100 determines the time between the end of the first bed period and the start of the next bed period is less than the maximum out-of-bed period. In one embodiment, a typical value for maximum out-of-bed period (MAX_UP_TIME) is 8 minutes (e.g., $8*60*F_S$ samples). If "no," the wireless sensor device does not combine the two bed periods and the process ends, via step 510. If "yes," the wireless sensor device 100 sets bed_entry [m+1]=bed_entry[m], and removes the bed period m, via step 516. This sets the bed entry time of the second bed period to be the bed entry time of the first bed period, essentially combining the bed periods. Next, the wireless sensor device 100 removes bed period m, and increments the current bed period, m=m+1, via step 518, and returns to step 504. An example diagram showing two combined bed periods is shown in FIGS. 7A and 7B below.

Figure 6:
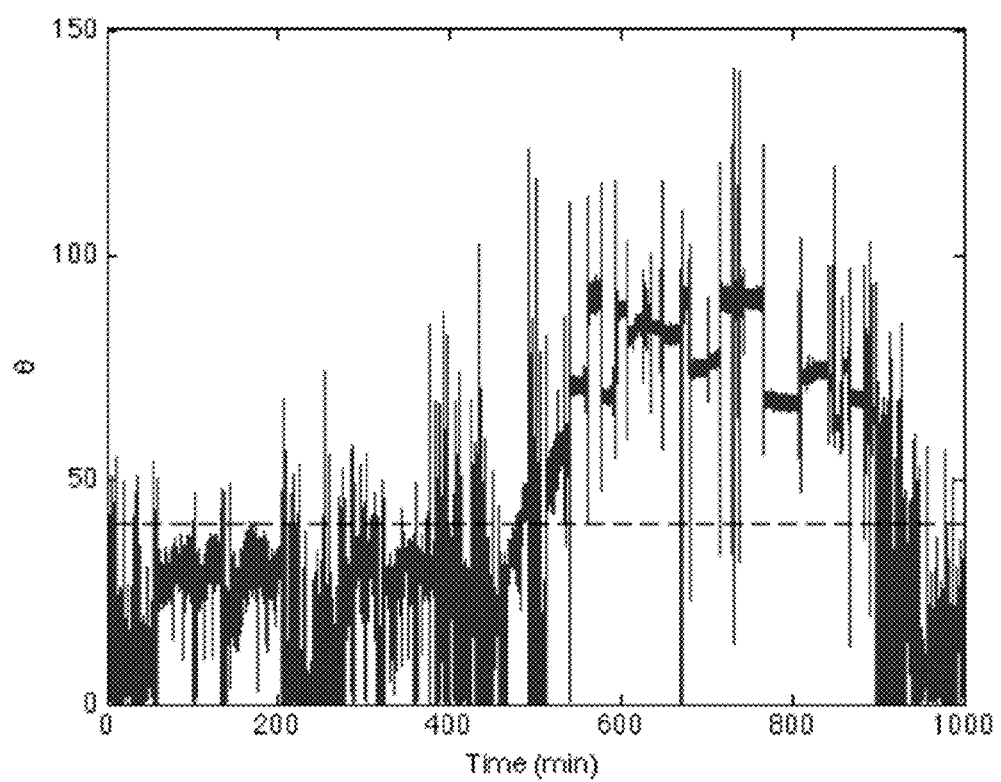
FIG. 6 illustrates a diagram of an example of showing polar angles versus time in accordance with an embodiment.

FIG. 6 illustrates a diagram 600 of an example of showing polar angles versus time in accordance with an embodiment. As shown, the dashed line is the threshold for lying down. Whenever the polar angle goes above the threshold, the wireless sensor device 100 determines that the person is lying down. As shown, the time period from 500 minutes to 900 minutes is the bed time.

Figure 7A:
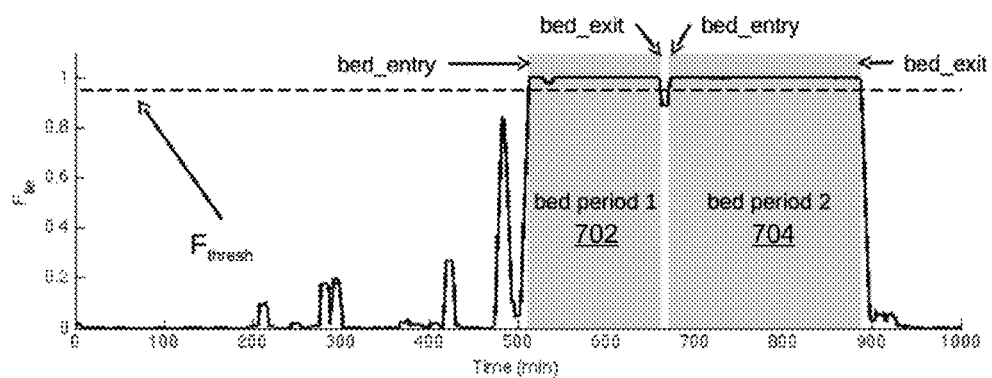
FIG. 7A illustrates a diagram of an example of two bed periods 702 and 704 in accordance with an embodiment.
Figure 7B:
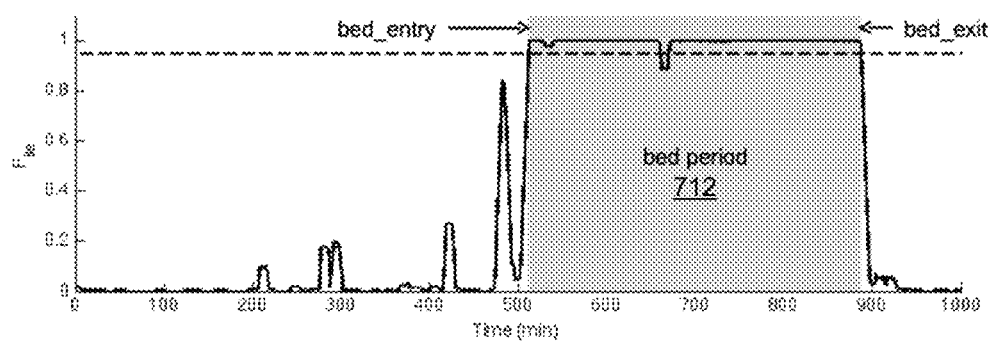
FIG. 7B illustrates a diagram of an example of a combined bed period 712 in accordance with an embodiment.

FIG. 7A illustrates a diagram 700 of an example of two bed periods 702 and 704 in accordance with an embodiment. As shown, the bed period 702 has a bed entry time and a bed exit time. Bed period 704 also has a bed entry time and a bed exit time.

Diagram 700 also shows values of $F_{lie}$ relative to $F_{thresh}$. As shown, in this example, once $F_{lie}$ crosses above $F_{thresh}$ for more that 95 percent of a window T, the wireless sensor device 100 determines the window T as a bed period. In this particular example, the wireless sensor device 100 detects two bed periods. Also, in this particular example, the little sliver of white between the two bed periods 702 and 704 is less than 8 minutes. As such, the wireless sensor device 100 would combine the two bed periods 702 and 704 as described below in connection with FIG. 7B.

FIG. 7B illustrates a diagram 710 of an example of a combined bed period 712 in accordance with an embodiment. Diagram 710 shows an example where the wireless sensor device 100 has combined two bed periods.

As shown, the bed entry time of the bed period 712 is the same as the bed entry time of the bed period 702 of FIG. 7A. Also, the bed exit time of the bed period 712 is the same as the bed exit time of the bed period 704 of FIG. 7A.

Embodiments disclosed herein provide numerous benefits. For example, implementations of the embodiments described herein use a wireless sensor device such as an accelerometer that is mounted on the chest or torso of a person to measure a variety of sleep parameters that can be important for monitoring sleep patterns. Embodiments may use these parameters is useful for tracking aspects such as the general regularity of the sleep time over a course of days or months. These parameters can also be used to trigger start and end of algorithms that are run during sleep in order to understand and monitor general sleep patterns (e.g., tracking regularity and length of time in bed over time).

A wireless sensor device obtains acceleration samples in relation to one or more axes associated with a person's body over a predetermined time window. The wireless sensor device calculates a polar angle for each acceleration sample within the predetermined time window. Next, the wireless sensor device calculates a fraction of an amount of time within the predetermined time window that the polar angle is greater than an angle threshold that indicates that the person is lying down. In one embodiment, if the fraction is greater than a predetermined angle threshold, the predetermined time window is marked as a period the person is lying down.

A method and system for determining a time period a person is in bed has been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or computer-readable medium. The software application provides instructions that enable the processor to cause the receiver to perform the functions described herein.

Furthermore, embodiments may take the form of a computer program product accessible from a computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

The medium may be an electronic, magnetic, optical, electromagnetic, infrared, semiconductor system (or apparatus or device), or a propagation medium. Examples of a computer-readable medium include a semiconductor or solid state memory, magnetic tape, a removable computer diskette, a random access memory (RAM), a read-only memory (ROM), a rigid magnetic disk, and an optical disk. Current examples of optical disks include DVD, compact disk-read-only memory (CD-ROM), and compact disk-read/write (CD-RAN).

Although the present invention has been described in accordance with the embodiments shown, one of ordinary skill in the art will readily recognize that there could be variations to the embodiments, and those variations would be within the spirit and scope of the present invention. Accordingly, many modifications may be made by one of ordinary skill in the art without departing from the spirit and scope of the appended claims.

What is claimed is:

1. A computer-implemented method for determining a time period a person is in bed, the method comprising:
   utilizing a wireless sensor device to obtain a plurality of acceleration samples in relation to at least one axis associated with a person's body over a predetermined time window;
   calculating a polar angle for each acceleration sample within the predetermined time window; and
   calculating a fraction of an amount of time within the predetermined time window that the polar angle is greater than an angle threshold that indicates that the person is lying down, wherein if the fraction is greater than a predetermined angle threshold, the predetermined time window is marked as a period the person is lying down.

2. The method of claim 1, wherein the plurality of acceleration samples are calibrated.

3. The method of claim 1, the obtaining of the plurality of acceleration samples comprises:
  obtaining raw acceleration samples in relation to the at least one axis; and
  determining the plurality acceleration samples based on calibrated raw acceleration samples.

4. The method of claim 1, wherein the at least one axis includes a plurality of axes in relation to the person's body.

5. The method of claim 1, wherein the at least one axis includes one or more of an X-axis, a Y-axis, and a Z-axis in relation to the person's body.

6. The method of claim 1, wherein the at least one axis includes an X-axis, a Y-axis, and a Z-axis.

7. The method of claim 1, wherein the at least one axis includes a mediolateral axis, a vertical axis, and an anteroposterior axis.

8. The method of claim 1, wherein the wireless sensor device is at least one of a triaxial accelerometer, a uni-axial accelerometers, a bi-axial accelerometers, a gyroscope, and a pressure sensor.

9. The method of claim 1, wherein the predetermined time window is a bed period having a bed entry time and a bed exit time.

10. The method of claim 1, wherein the predetermined time window is a first bed period, wherein the method further comprises combining the first bed period with a second bed period if an out-of-bed period between the first bed period and second bed period meets a combine threshold.

11. A wireless sensor device for determining a time period a person is in bed, comprising:
  a processor; and
  a memory device coupled to the processor, wherein the wireless sensor device includes an application that, when executed by the processor, causes the processor to perform operations comprising:
    obtaining a plurality of acceleration samples in relation to at least one axis associated with a person's body over a predetermined time window utilizing a wireless sensor device to obtain the plurality of acceleration samples;
    calculating a polar angle for each acceleration sample within the predetermined time window; and
    calculating a fraction of an amount of time within the predetermined time window that the polar angle is greater than an angle threshold that indicates that the person is lying down, and wherein if the fraction is greater than a predetermined angle threshold, the predetermined time window is marked as a period the person is lying down.

12. The wireless sensor device of claim 11, wherein the plurality of acceleration samples are calibrated.

13. The wireless sensor device of claim 11, the obtaining of the plurality of acceleration samples comprises:
  obtaining raw acceleration samples in relation to the at least one axis; and
  determining the plurality acceleration samples based on calibrated raw acceleration samples.

14. The wireless sensor device of claim 11, wherein the at least one axis includes a plurality of axes in relation to the person's body.

15. The wireless sensor device of claim 11, wherein the at least one axis includes one or more of an X-axis, a Y-axis, and a Z-axis in relation to the person's body.

16. The wireless sensor device of claim 11, wherein the at least one axis includes an X-axis, a Y-axis, and a Z-axis.

17. The wireless sensor device of claim 11, wherein the at least one axis includes a mediolateral axis, a vertical axis, and an anteroposterior axis.

18. The wireless sensor device of claim 11, wherein the wireless sensor device is at least one of a triaxial accelerometer, a uni-axial accelerometers, a bi-axial accelerometers, a gyroscope, and a pressure sensor.

19. The wireless sensor device of claim 11, wherein the predetermined time window is a bed period having a bed entry time and a bed exit time.

20. The wireless sensor device of claim 11, wherein the predetermined time window is a first bed period, wherein the method further comprises combining the first bed period with a second bed period if an out-of-bed period between the first bed period and second bed period meets a combine threshold.

* * * * *